United States Patent

Sugie et al.

[11] 4,125,731
[45] Nov. 14, 1978

[54] NOVEL INDAN DERIVATIVES

[75] Inventors: Akihiko Sugie, Takarazuka; Hiromi Shimomura, Nishinomiya; Junki Katsube, Toyonaka; Hisao Yamamoto, Kobe, all of Japan

[73] Assignee: Sumitomo Chemical Company, Limited, Osaka, Japan

[21] Appl. No.: 748,539

[22] Filed: Dec. 8, 1976

[30] Foreign Application Priority Data

Dec. 23, 1975 [JP] Japan .................. 50-154485
Dec. 23, 1975 [JP] Japan .................. 50-154486
Jun. 4, 1976 [JP] Japan .................. 51-65982

[51] Int. Cl.² .......................................... C07C 69/76
[52] U.S. Cl. .................. 560/53; 260/343.3 P; 260/346.71; 260/345.7 R; 424/308; 560/56; 260/345.8 R; 562/462; 562/466
[58] Field of Search .................. 560/53, 56; 424/308; 260/520 D

[56] References Cited

U.S. PATENT DOCUMENTS 3,704,314 11/1972 Cragoe et al. .................. 560/53
3,974,212 8/1976 Cragoe et al. .................. 560/53

Primary Examiner—Paul J. Killos

Attorney, Agent, or Firm—Stevens, Davis, Miller & Mosher

[57] ABSTRACT

Novel indan compounds of the formula

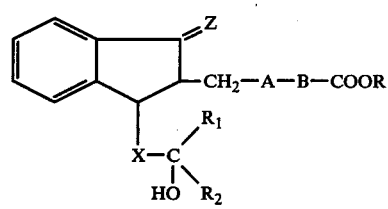

wherein A and X are each ethylene or vinylene; B is $C_{2-4}$ alkylene; R and $R_2$ are each hydrogen or $C_{1-4}$ alkyl; $R_1$ is $C_{1-8}$ alkyl; $<C = Z$ is $<C = O$, or

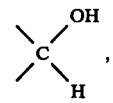

and its non-toxic salts, which are useful as antiulcers, gastric secretion inhibitors, and hypotensors.

6 Claims, No Drawings

NOVEL INDAN DERIVATIVES

The present invention relates to novel indan compounds and to their production and use.

More particularly, this invention relates to novel indan compounds, to a pharmaceutical composition containing at least one of the indan compounds and to a process for their preparation. The novel indan compounds of this invention is representable by the following formula (I);

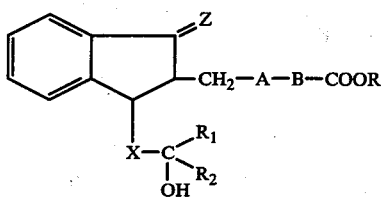

wherein A and X are each ethylene or vinylene; B is $C_{2-4}$ alkylene; R and $R_2$ are each hydrogen or $C_{1-4}$ alkyl; $R_1$ is $C_{1-8}$ alkyl; and $<C = Z$ is $<C = O$ or

and its non-toxic salt when R is hydrogen.

In the significance as used above, "$C_{2-4}$ alkylene" means an alkylene having 2 to 4 carbon atoms, of which preferred examples are ethylene, propylene and butylene. "$C_{1-8}$ alkyl" means a straight or branched alkyl group having from one to eight carbon atoms (e.g., methyl, pentyl, α-methyl-n-pentyl, α,α-dimethyl-n-pentyl). The indan compounds [I] of this invention have various useful pharmacological activities and are useful as antiulcer agents, gastric secretion inhibitors, and hypotensors.

The indan compounds [I] have been found to possess anti-gastro-intestinal ulcer activity. That is, they inhibit an excessive secretion of gastric acid, and thereby inhibit formation of gastro-intestinal ulcer or heal the ulcer in mammals.

The compounds [I] also show a hypotensive activity. Among the indan compounds [I] of this invention, the compounds of the following formula [Ia] are preferable;

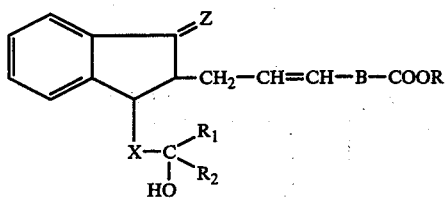

wherein B, X, R, $R_1$, $R_2$ and Z are as defined above, for instance, in view of their excellent properties as gastric secretion inhibitors. Particular preferred are the compounds of the following formula [Ib];

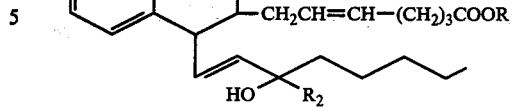

wherein R and $R_2$ are as defined above.

The novel indan compounds [I] of the invention can be prepared by the following methods:

Method (a):

The novel indan compound [Ic] of the formula:

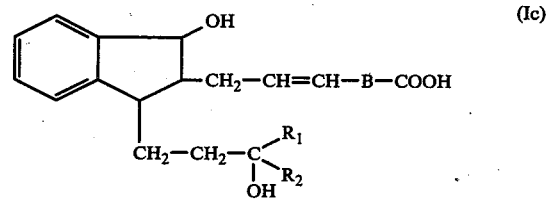

wherein B, $R_1$ and $R_2$ are as defined above, can be prepared by reacting the compound of the formula [II];

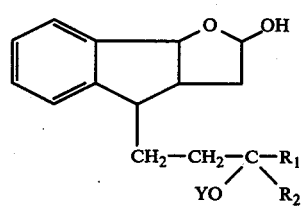

wherein $R_1$ and $R_2$ are as defined above and Y is hydrogen or a hydroxy protecting group, with a compound of the formula [III];

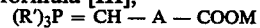

$$(R')_3P = CH - A - COOM \qquad [III]$$

wherein A is as defined above, R' is an aryl and M is an alkali metal and, if Y is a hydroxy-protecting group, such as tetrahydropyranyl, or alkoxyalkyl, hydrolyzing the resulted products. The Wittig reaction can be carried out in the presence of solvent using 1 - 10 equivalent (preferably 2 - 4 equivalent) of the Wittig reagent [III]. Examples of the solvent are ethers (e.g. diethylether, tetrahydrofuran, dioxane, dimethoxyethane), hydrocarbons (e.g., benzene, toluene, hexane) and dimethyl sulfoxide. The reaction can be effected ordinally at room temperature, but it can be controlled with warming or cooling depending upon the extent of the progress. The reaction time may vary depending upon the reaction temperature and the reagent to be used therein but generally 2 - 30 hrs. The Wittig reagent [III] can be prepared by reacting a compound of the formula [III-a]:

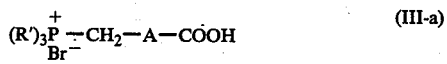

with a base according to known method [E. J. Corey, J. Amer. Chem. Soc., 91 5675 (1969)]. The indan compound thus obtained can be separated from the reaction mixture and the indan compound thus obtained, if Y is a hydroxy-protecting group, can be hydrolyzed and purified by the conventional procedures.

Method (b):

The novel indan compound [Id] of the formula;

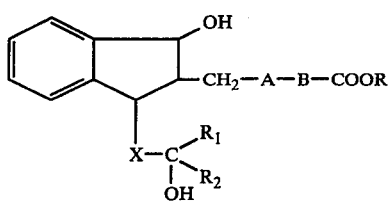

wherein A, B, X, R, $R_1$ and $R_2$ are as defined above, can be prepared by reducing a carbonyl compound of the formula [IV];

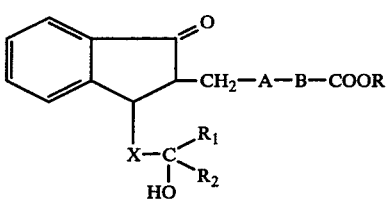

wherein A, B, X, R, $R_1$ and $R_2$ are as defined above, with a reducing agent and, when $R_2$ is hydrogen in the formula [Id], can be also prepared by reducing a carbonyl compound of the formula [V];

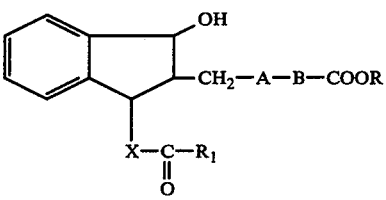

wherein A, B, X, R and $R_1$ are as defined above, with a reducing agent. For this reduction, any of known reducing agents which can reduce only ketonic carbonyl group without affecting ester or acid groups or carbon-carbon double bonds can be used. Examples of such reducing agents are the metal borohydrides, especially sodium, potassium, and zinc borohydrides, lithium (tri-tertbutoxy)aluminum hydride, metal trialkoxy borohydrides, e.g., sodium trimethoxyborohydride, aluminum alkoxide, e.g., aluminum isopropoxide, aluminum ethoxide. The reaction can be carried out in the presence of inert solvent (e.g. alcohol, dioxane, tetrahydrofuran, dimethoxyethane). The reaction condition may vary depending upon the reaction temperature and the reducing agent to be used therein.

The reaction temperature may be from −20° to 20° C. The indan compound thus obtained can be separated from the reaction mixture and purified by the conventional procedures.

Method (c):

The novel indan compound [Ie] of the formula:

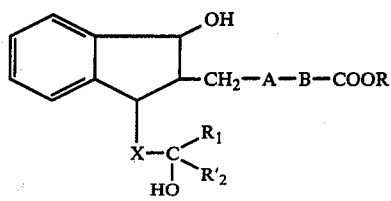

wherein A, B, X, R and $R_1$ are as defined above and $R'_2$ is a $C_{1-4}$ alkyl group, can be prepared by reacting a compound of the formula [VI];

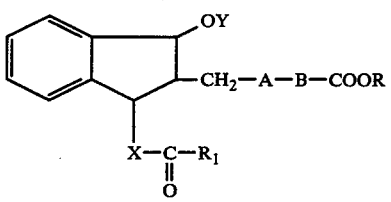

wherein A, B, X, R, $R_1$ and Y are as defined above, with a compound of the formula [VII];

$$R_2' - M' \qquad [VII]$$

wherein $R_2'$ is as defined above, and M' is magnesium halide or alkali metal and if Y is a hydroxy-protecting group, hydrolyzing the resulted products. The reaction can be carried out in the presence of inert solvent by using the 1 − 1.5 equivalent organic metal compound.

Examples of the inert solvent are ethers (e.g., diethylether, tetrahydrofuran, dimethoxyethane) and hydrocarbons (e.g., benzene, toluene).

The organic metal compound can be prepared by the conventional procedures. The reaction condition may vary depending upon the reaction temperature and the organic metal compound to be used therein, but the temperature is preferably about 0°− 10° C to avoid side reaction. The novel indan compound thus obtained can be separated, if Y is a hydroxy-protecting group, hydrolyzed and purified by the conventional procedures.

Method (d):

The novel indan compound [If] of the formula

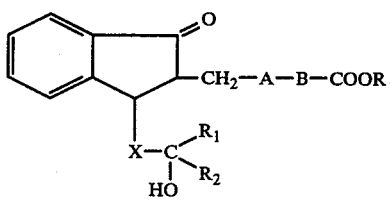

wherein A, B, X, R, $R_1$ and $R_2$ are as defined above, can be prepared by oxidizing a hydroxy compound of the formula [VIII]

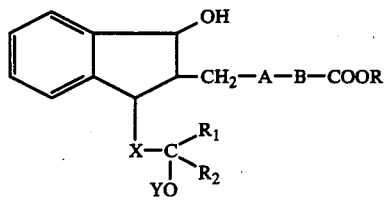

(VIII)

wherein A, B, X, R, $R_1$, $R_2$ and Y are as defined above, with oxidizing agent. For this oxidation, any of known oxidizing agents which can oxidize only secondary alcohol group without affecting ester or carbon-carbon double bonds can be used. Examples of such oxidizing agents are manganese dioxide, anhydrous chromic acid, anhydrous chromic acid-pyridin (Collins reagent), and organic oxidizer such as N-bromoacetamide or dimethylsulfoxidedicyclohexylcarbodiimide (Moffatt oxidation). The reaction can be carried out in the presence or absence of solvent. Examples of the solvent are dichloromethane, chloroform, carbon. tetrachloride, acetic acid or t-butanol. The reaction condition may vary depending upon the reaction temperature and the oxidizing agent to be used therein. The reaction temperature may be from $-10°$ to $50°$ C. The indan compound thus obtained can be separated from the reaction mixture and, if Y is a hydroxy-protecting group, hydrolyzed and purified by the conventional procedures.

Among the indan compounds [I] thus obtained, the carboxylic acid compound (R = H) can be transformed to its pharmacologically acceptable salt form.

The pharmacologically acceptable salts of these indan compounds are those with pharmaceutically acceptable metal cations such as, sodium, potassium, magnesium and calcium, ammonium or amine cations. The novel indan compounds of this invention may be administered effectively orally, sublingually, or by intravenous, intramuscular, or subcutaneous injection at a daily dosage of about 1 to 100 mg/kg as gastric secretion inhibitors and antiulcer, and about 1 to 20 mg/kg as hypotensives.

Starting materials of this invention are prepared by the reactions and procedures described and exemplified hereinafter. The indan compounds of the formulae [II], [IV], [V], [VI] and [VIII] are each prepared by the sequence of transformations shown in charts A and B.

Chart A

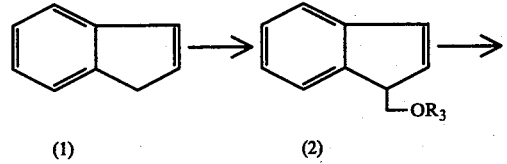

(1) (2)

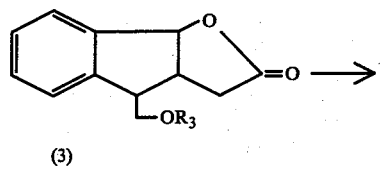

(3)

Chart A (continued)

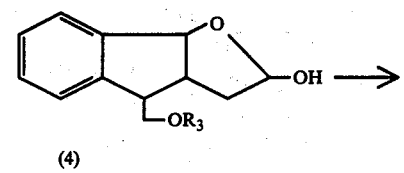

(4)

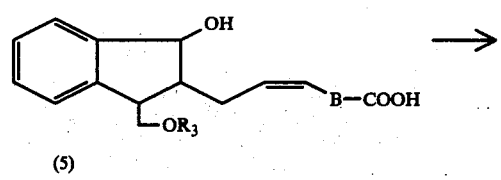

(5)

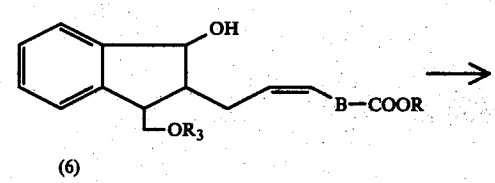

(6)

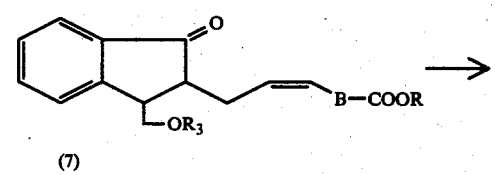

(7)

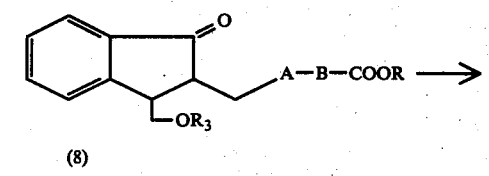

(8)

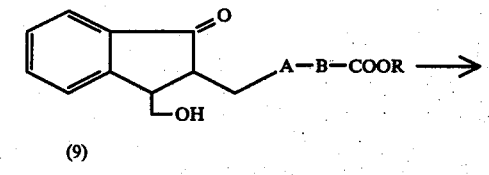

(9)

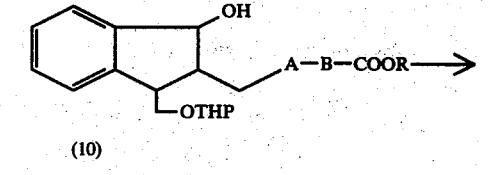

(10)

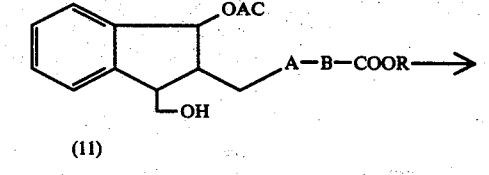

(11)

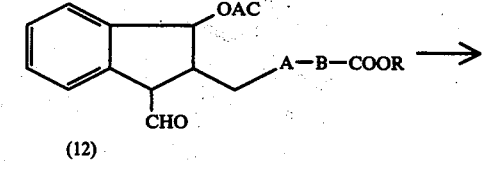

(12)

-continued
Chart A

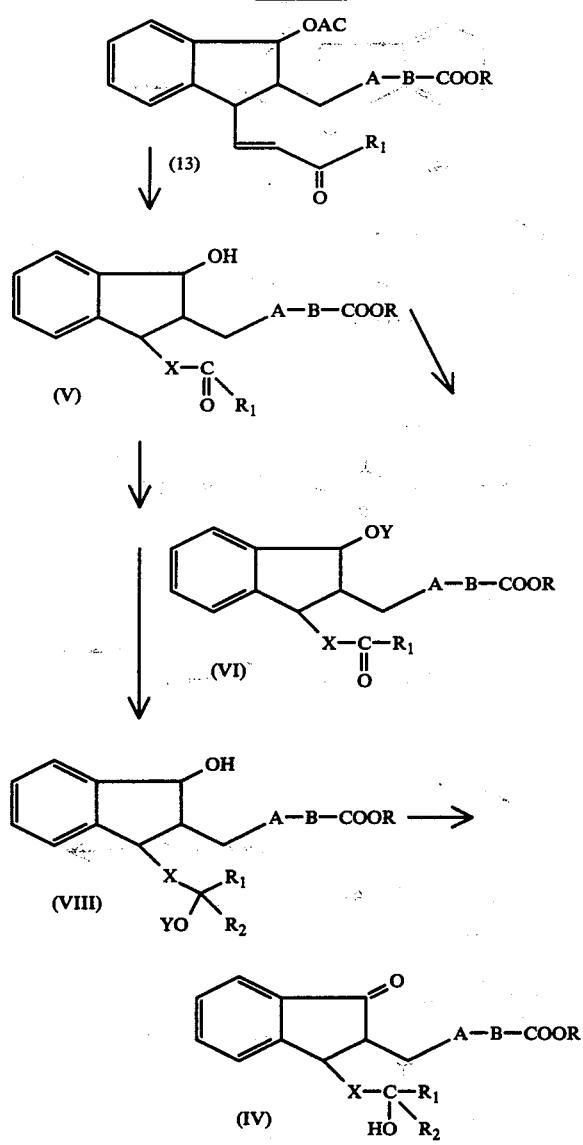

wherein $R_1$, $R_2$, A, B, R, X and Y are as defined above. THP is tetrahydropyranyl, AC is acetyl, and $R_3$ is methyl of benzyl.

Chart B

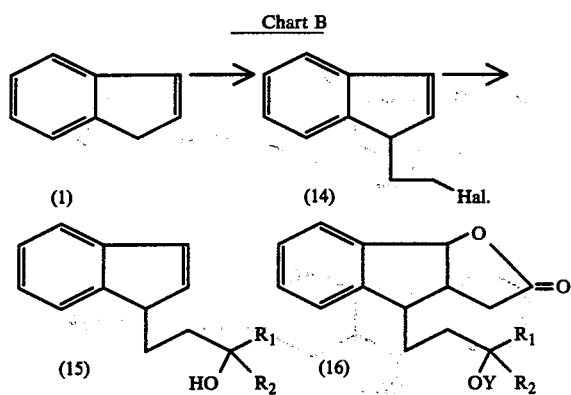

-continued
Chart B

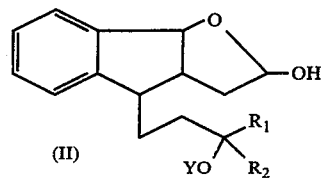

wherein $R_1$, $R_2$ and Y are as defined above, and Hal. is halogen atom.

The compound (3) was obtained from indene (1) by a sequence of alkylation and lactonization. The compound (3) was reduced with diisobutylaluminum hydride to afford the hemiacetal (4), which was reacted with the Wittig reagent to give the compound (5). The compound (5) was further esterified to give the compound (6), which was oxidized to give the keto compound (7) and, if necessary, the compound (7) was reduced to give the compound (8). The compound (11) was obtained from the compound (8) by a sequence of dealkylation, hydroxy-protection and reduction. The compound (11) was oxidized to give the aldehyde compound (12), which was treated with the Wittig reagent to give the enone (13). The compound (13) was derived to the compound (V) by the conventional procedure. The transformations of indene (1) to the compound (II) are shown in Chart B. The compound (15) was obtained from indene by alkylation and Grignard reaction. The transformations of the compound (15) to the compound (II) was accomplished by lactonization, if necessary, hydroxy-protection, and reduction. The indan compounds of this invention have three centers of asymmetry. They can be, however, encompassed by all stereoisomers.

The following examples are given for the purpose of illustration and it is not intended to limit the invention.

[EXPERIMENT]

The IR spectra were taken with a spectrometer Hitachi 285 (Hitachi Co.). The NMR spectra were recorded on a Varian A-60 spectrophotomer with TM9 as internal standard.

EXAMPLE 1

To a solution of indane (240 g) in dry ether (1 l) was slowly added, with stirring under a nitrogen atmosphere, 2.2 M solution (1 l) of n-butyllithium in n-hexane at −40° C over an hour. After 15 minutes, to this solution was added chloromethyl methyl ether (170 g) in dry ether (150 ml) under nitrogen at −55° C over 30 minutes. After stirring for another 30 minutes, water (1 l) was added with efficient stirring. The ether layer was separated, the aqueous phase extracted with ether (100 ml) twice, and the combined ether extract was washed with brine and dried over $MgSO_4$. The ether was evaporated and the residual oily substance was distilled to give 1-methoxymethyl indene as yellow oil. (b.p. 50° C/0.2 mmHg, 258 g yield 78%)

A mixture of acetic acid (1 l), acetic anhydride (500 ml), 1-methoxymethyl indene (64 g) and manganic (III) acetate (214 g) was heated to reflux for 1 hr. under nitrogen. After cooling manganese (II) acetate was removed by filtration and washed with ethyl acetate. The filtrate was concentrated under reduced pressure. The residue was dissolved in ethylacetate and was washed with water, and aqueous sodium bicarbonate, dried and concentrated in vacuo to give a crude mixture, which was chromatographed on silica gel to afford a yellow oily 3-methoxymethyl-1-hydroxy-2-indan-acetic acid-γ-lactone (59 g, yield 68%)

IR$\gamma_{max}^{film}$; 1775, 1605, 1160 cm$^{-1}$

To a solution of 3-methoxymethyl-1-hydroxy-2-indan-acetic acid-γ-lactone (1.0 g) in dry toluene (30 ml) cooled to −60° C, was added dropwise diisobutylaluminium hydride (1.3 g) in toluene under nitrogen. Stirring and cooling was continued for 20 minutes, and then aqueous ammonium chloride was cautiously added. The mixture was filtered and the filtrate was washed with brine, dried and concentrated to afford an oily hemiacetal (950 mg, yield 95%)

IR$\gamma_{max}^{film}$; 3400, 1600, 1120, 1025 cm$^{-1}$

A suspension of 50% sodium hydride (917 mg) in anhydrous dimethyl sulfoxide (DMSO, 10 ml) was stirred for 1 hr. at 70° – 75° C under nitrogen and cooled to ambient temperature. To this solution was added 4.06 g of 4-carboxy-n-butyl-triphenylphosphonium bromide in DMSO (10 ml). After stirring 5 minutes, a solution of 950 mg of 3-methoxymethyl-1-hydroxy-indan-2-acetoaldehyde-γ-lactol prepared above in DMSO (10 ml) was added and the resulting mixture was allowed to stir overnight at room temperature. The reaction mixture was quenched by addition to a mixture of ice-water and ether. After equilibration, the organic pulse was washed with 1N sodium hydroxide and water. The aqueous washings were combined and carefully acidified with hydrochloric acid. The aqueous phase was extracted well with ether. The organic extract was washed with water, dried, and evaporated in vacuo. The residue was dissolved in tetrahydrofuran and treated with excess ethereal diazomethane. After evaporation, the crude product was chromatographed on silica gel to give 3-methoxymethyl-2-(6'-carbomethoxy-2'-cis-hexenyl)-indan-1-ol (1.2 g) as faint yellow oil.

IR$\gamma_{max}^{film}$: 3450, 1735, 1605, 1110 cm$^{-1}$

EXAMPLE 2

Active manganese dioxide (7 g) was added to a solution of 3-methoxymethyl-2-(6'-carbomethoxy-2'-cis-hexenyl)-indan-1-ol (1.21 g) in dry toluene (20 ml). The resulting mixture was stirred overnight and filtered. The filtrate was evaporated to give 3-methoxymethyl-2-(6'-carbomethoxy-2'-cis-hexenyl)-indan-1-one (1.18 g) as yellow oil.

IR$\gamma_{max}^{film}$: 1735, 1710, 1605 cm$^{-1}$

EXAMPLE 3

A mixture of 75 mg of 3-methoxymethyl-2-(6'-carbomethoxy-2'-cis-hexenyl)-indan-1-ol and 20 mg of 5% Pd-C in 10 ml of ethanol was stirred for 2 hrs. at room temperature under 1 atom of hydrogen. The mixture was filtered and the filtrate to give an oily 3-methoxymethyl-2-(6'-carbomethoxyhexyl)-indan-1-ol (70 mg), which was oxidized as the same procedures described in example 2 to afford 68 mg of 3-methoxymethyl-2-(6'-carbomethoxyhexyl)-indan-1-one as yellow oil.

IR$\gamma_{max}^{film}$: 1735, 1710, 1605 cm$^{-1}$

EXAMPLE 4

To a stirred solution of 980 mg of 3-methoxymethyl-2-(6'-carbomethoxy-2'-cis-hexenyl)-indan-1-one in 50 ml of ethylacetate was added carefully a solution of 4.3 g of boron tribromide in 20 ml of chilled ethylacetate under nitrogen at 0° C. After stirring for 10 hrs. at the same temperature, to this was added saturated sodium bicarbonate. The organic layer was separated and the aqueous phase was extracted well with ethylacetate. The organic extracts were combined, washed with brine and dried over sodium sulfate.

After evaporation, the residue was chromatographed on silica gel to give 890 mg of 3-hydroxymethyl-2-(6'-carbomethoxy-2'-cis-hexenyl)-indan-1-one as faint yellow oil.

IR$\gamma_{max}^{film}$: 3400, 1735, 1710, 1605 cm$^{-1}$

Following the procedures of Example 4, 3-hydroxymethyl-2-(6'-carbomethoxy-hexyl)-indan-1-one was obtained.

IR$\gamma_{max}^{film}$: 3400, 1735, 1710, 1605 cm$^{-1}$

EXAMPLE 5

To a mixture of 1.19 g of 3-hydroxymethyl-2-(6'-carbomethoxy-2'-cis-hexenyl)-indan-1-one and 400 mg of 2,3-dihydropyran in 50 ml of methylene chloride was added 50 mg of p-toluene sulfonic acid at 0° C. After stirring for 10 minutes at 0° C and then for 40 minutes at room temperature, the reaction solution was quenched by addition of aqueous sodium bicarbonate. The resulting mixture was extracted well with chloroform. The organic extracts were combined, washed with brine, dried over sodium sulfate, and evaporated to give 1.9 g of 3-tetrahydropyranyloxymethyl-2-(6'-carbomethoxy-2'-cis-hexenyl)-indan-1-one as oil.

IR$\gamma_{max}^{film}$: 1740, 1715, 1605 cm$^{-1}$

To a solution of 1.9 g of tetrahydropyranylether prepared above in 30 ml of methanol at 0° C under nitrogen was added a solution of 480 mg of sodium borohydride in 20 ml of chilled methanol. After 1 hr. the reaction solution was quenched by addition of 10 ml of acetone.

The resulting mixture was allowed to warm to room temperature and then evaporated to give a sirupy residue, which was poured onto a chilled aqueous solution of ammonium chloride. The resulting organic layer was extracted with ethylacetate. The organic layer was washed with brine, dried over magnesium sulfate and evaporated to give 3-tetrahydropyranyloxymethyl-2-(6'-carbomethoxy-2'-cis-hexenyl)-indan-1-ol as oil.

IR$\gamma_{max}^{film}$: 3400, 1740 cm$^{-1}$

A solution of 1.6 g of indan alcohol derivative prepared above, 5 ml of dry pyridine and 800 mg of acetic anhydride was stirred at room temperature over night. The resulting mixture was diluted with benzene and heated for 3 hrs. at 70° C. The reaction mixture was poured into ice-water. The resulting mixture was extracted well with ethylacetate. The organic layer was washed with aqueous sodium bicarbonate, dried over magnesium sulfate and evaporated to give 1.8 g of 3-tetrahydropyranyloxymethyl-2-(6'-carbomethoxy-2'-cis-hexenyl)-1-acetoxy-indan as oil.

IR$\gamma_{max}^{film}$: 1740, 1240 cm$^{-1}$

The 1.8 g of acetoxy indan prepared above was dissolved in 27 ml of a solution of acetic acid-water-tetrahydrofuran (5:2:2) and heated at 60° C for 11 hrs. The reaction mixture was diluted with water, and extracted with ether. The extract was washed with aqueous sodium bicarbonate, dried over magnesium sulfate and evaporated to give an oily residue, which was chromatographed on silica gel to afford 930 mg of 3-hydroxymethyl-2-(6'-carbomethoxy-2'-cis-hexenyl)-1-acetoxy-indan as faint yellow oil.

IR$\gamma_{max}^{film}$: 3400, 1735 cm$^{-1}$

Following the procedures of Example 5, 3-hydroxymethyl-2-(6'-carbomethoxy-hexyl)-1-acetoxy-indan was obtained.

IR$\gamma_{max}^{film}$: 3400, 1735 cm$^{-1}$

EXAMPLE 6

To a stirred mixture of 500 mg of anhydrous chromium trioxide and 15 ml of methylene chloride under nitrogen and cooled at 0° C was added 1 g of anhydrous pyridine. The resulting mixture was stirred for 15 minutes at 0° C and at room temperature for another 2 hrs. and then at 0° C again. A cold (10° C) solution of 175 mg of 3-hydroxymethyl-2-(6'-carbomethoxy-2'-cis-hexenyl)-1-acetoxy indan in 5 ml of methylene chloride was added rapidly to the solution. After 15 minutes additional stirring, 20 ml of dry benzene was added. The mixture was filtered through Celite, washing with benzene. The filtrate was evaporated to give 3-formyl-2-(6'-carbomethoxy-2'-cis-hexenyl)-1-acetoxy-indan.

To a stirred mixture of 100 mg of sodium hydride (50% dispersion in mineral oil) and 10 ml of tetrahydrofuran under nitrogen at 0° C was added 444 mg of dimethyl 2-oxoheptyphosphonate, The cooling bath was removed and the mixture was stirred at room temperature for 2 hrs. and then cooled to 0° C again.

To this was added a solution of 170 mg of aldehyde prepared above in 10 ml of tetrahydrofuran. Stirring was continued at room temperature for 3 hrs. After addition of 200 mg of acetic acid, the resulting mixture was concentrated under reduced pressure. The residue was dissolved in benzene. The benzene solution was washed with aqueous sodium bicarbonate, and brine, dried over sodium sulfate and concentrated under reduced pressure. The residue was purified by chromatography on silica gel to give 120 mg of 3-(3'-oxo-1'-trans-octenyl)-2-(6'-carbomethoxy-2'-cis-hexenyl)-1-acetoxy-indan as light yellow oil.

IR$\gamma_{max}^{film}$: 1740, 1695, 1630 cm$^{-1}$

Following the procedures of Example 6, 3-(3'-oxo-1'-trans-octenyl)-2-(6'-carbomethoxyhexyl)-1-acetoxy-indan, IR$\gamma_{max}^{film}$: 1740, 1695, 1630 cm$^{-1}$ and 3-(4',4'-dimethyl-3'-oxo-1'-trans-octenyl)-2-(6'-carbomethoxy-2'-cis-hexenyl)-1-acetoxy-indan were obtained.

IR$\gamma_{max}^{film}$: 1740, 1695, 1625, 1235 cm$^{-1}$

EXAMPLE 7

To a solution of 60 mg of sodium borohydride in 8 ml of methanol cooled at −20° C under nitrogen was added a solution of 120 mg of 3-(3'-oxo-1'-trans-octenyl)-2-(6'-carbomethoxy-2'-cis-hexenyl)-1-acetoxy-indan in 5 ml of methanol. After 25 minutes, 10 ml of acetone was added and the mixture was allowed to warm to room temperature and then concentrated under reduced pressure to give a sirupy residue, which was diluted with ethylacetate. The organic layer was washed with saturated aqueous ammonium chloride, water and brine, dried over magnesium sulfate and evaporated to give 120 mg of 3-(3'-hydroxy-1'-trans-octenyl)-2-(6'-carbomethoxy-2'-cis-hexenyl)-1-acetoxy-indan.

IR$\gamma_{max}^{film}$: 3400, 1740, 1235 cm$^{-1}$

Following the procedures of Example 7, 3-(3'-hydroxy-1'-trans-octenyl)-2-(6'-carbomethoxy-hexyl)-1-acetoxy-indan, IR$\gamma_{max}^{film}$: 3400, 1740, 1240 cm$^{-1}$ and 3-(4',4'-dimethyl-3'-hydroxy-1'-trans-octenyl)-2-(6'-carbomethoxy-2'-cis-hexenyl)-1-acetoxy-indan were obtained.

IR$\gamma_{max}^{film}$: 3500, 1740, 1240, 1030 cm$^{-1}$

EXAMPLE 8

To a stirred solution of 210 mg of 3-(3'-oxo-1'-trans-octenyl)-2-(6'-carbomethoxy-2'-cis-hexenyl)-1-acetoxy-indan in 15 ml of tetrahydrofuran was added at −78° C under nitrogen was added dropwise an ethereal solution of methyl magnesium iodide prepared from 220 mg of magnesium metal and 1.28 g of methyl iodide in 10 ml of ether.

After 30 minutes, the reaction mixture was poured into aqueous ammonium chloride and extracted well with ether. The ether extracts were combined, washed with brine, dried over magnesium sulfate and evaporated. The residue was purified by chromatography on silica gel to give 150 mg of 3-(3'-methyl-3'-hydroxy-1'-trans-octenyl)-2-(6'-carbomethoxy-2'-cis-hexenyl)-1-acetoxy-indan as faint yellow oil.

IR$\gamma_{max}^{film}$: 3450, 1740, 1110, 1030 cm$^{-1}$

EXAMPLE 9

A mixture of 50 mg of 3-(3'-hydroxy-1'-transoctenyl)-2-(6'-carbomethoxy-2'-cis-hexenyl)-1-acetoxy-indan, 10 ml of solution of methanol-water (10:1) and 100 mg of potassium carbonate was stirred overnight at room temperature, and then concentrated under reduced pressure to give the residue, to which was added water and ether. After equilibration, the organic phase was washed with water. The aqueous washings were combined and carefully acidified with 2 M potassium bisulfate in the presence of ether. After equilibration, the aqueous phase was extracted well with ethylacetate. The organic extracts were combined dried over magnesium sulfate and evaporated to give 40 mg of 3-(3'-hydroxy-1'-trans-octenyl)-2-(6'-carboxy-2'-cis-hexenyl)-indan-1-ol as faint yellow oil.

IR$\gamma_{max}^{film}$: 3400, 2650, 1710 cm$^{-1}$

Following the procedures of Example 9, 3-(3'-hydroxy-1'-trans-octenyl)-2-(6'-carboxy-hexyl)-indan 1-ol, IR$\gamma_{max}^{film}$: 3400, 2650, 1710 cm$^{-1}$ and 3-(4',4'-dimethyl-3'-hydroxy-1'-trans-octenyl)-2-(6'-carboxy-2'-cis-hexenyl)-indan-1-ol were obtained.

IR$\gamma_{max}^{film}$: 3400, 2700, 1710 cm$^{-1}$

EXAMPLE 10

To a mixture of 120 mg of 3-(3'-hydroxy-1'-trans-octenyl)-2-(6'-carbomethoxy-2'-cis-hexenyl)-1-acetoxy-indan and 90 mg of 2, 3 dihydropyran in 15 ml of methylene chloride cooled at 0° C was added 50 mg of p-toluene sulfonic acid.

After stirring for 10 minutes at 0° C and then for 30 minutes at room temperature, the reaction solution was quenched by addition of aqueous sodium bicarbonate. The resulting mixture was extracted well with chloroform. The organic extracts were combined, washed with brine, dried over sodium sulfate, and evaporated to give 170 mg of 3-(3'-tetrahydropyranyloxy-1'-trans-octenyl)-2-(7'-carbomethoxy-2'-cis-hexenyl)-1-acetoxy-indan as yellow oil.

IR$\gamma_{max}^{film}$: 1740, 1240 cm$^{-1}$

A mixture of 170 mg of tetrahydropyranylether prepared above and 200 mg of potassium carbonate in 10 ml of a solution methanol-water (10:1) was stirred over night at room temperature and then concentrated under reduced pressure. The residue was diluted with ether. The organic layer was washed with 2 N sodium hydroxide and water. The aqueous washings were combined and carefully acidified with 2 M potassium bisulfate in the presence of ether. After equilibration the aqueous phase was extracted well with ethylacetate. To this organic extracts was added an etheral solution of diazo methane and then the solution as concentrated to give a residue, which was purified with chromatography on alumina to afford 120 mg of 3-(3'-tetrahydropyranyloxy-1'-transoctenyl)-2-(6'-carbomethoxy-2'-cis-hexenyl)-indan-1-ol as faint yellow oil.

IR$\gamma_{max}^{film}$: 3400, 1740 cm$^{-1}$

Following the procedures of Example 10, 3-(3'-tetrahydropyranyloxy-1'-trans-octenyl)-2-(6'-carbomethoxy-hexyl)-indan-1-ol, IR$\gamma_{max}^{film}$: 3400, 1740 cm$^{-1}$ and 3-(4',4'-dimethyl-3'-tetrahydropyranyloxy-1'-transoctenyl)-2-(6'-carbomethoxy-2'-cis-hexenyl)-indan-1-ol were obtained.

IR$\gamma_{max}^{film}$: 3400, 1740, 1020 cm$^{-1}$

EXAMPLE 11

To a stirred mixture of 500 mg of anhydrous chromium trioxide and 15 ml of methylene chloride under nitrogen and cooled at 0° C was added 1 g of anhydrous pyridine. The resulting mixture was stirred for 15 minutes at 0° C and for another 2 hrs. at room temperature and then cooled at −20° C. A cold solution of 120 mg of 3-(3'-tetrahydropyranyloxy-1'-trans-octenyl)-2-(6'-carbomethoxy-2'-cis-hexenyl)-indan-1-ol in 5 ml of methylene chloride was added rapidly to this solution. After stirring for 15 minutes, 20 ml of benzene was added. The mixture was filtrated through Celite, washing with benzene and the filtrate was evaporated in vacuo to give a crude, oily substance, which was dissolved in 5 ml of a solution of acetic acid-water-tetrahydrofuran (3:1:1) and heated at 50° C for 8 hrs. The reaction mixture was evaporated almost to dryness. The residue was chromatographed on silica gel to give 85 mg of 3-(3'-hydroxy-1'-trans-octenyl)-2-(6'-carbomethoxy-2'-cis-hexenyl)-indan-1-one as faint yellow oil.

IR$\gamma_{max}^{film}$: 3400, 1735, 1715, 1605 cm$^{-1}$

Following the procedures of Example 11, following compounds were obtained. 3-(3'-hydroxy-1'-trans-octenyl)-2-(6'-carbomethoxy-hexyl)-indan-1-one, IR$\gamma_{max}^{film}$: 3400, 1740, 1715, 1605 cm$^{-1}$ 3-(4',4'-dimethyl-3'-hydroxy-1'-trans-octenyl)-2-(6'-carbomethoxy-2'-cis-hexenyl)-indan-1-one.

IR$\gamma_{max}^{film}$: 3450, 1740, 1720, 1605 cm$^{-1}$

EXAMPLE 12

To a stirred solution of 30 mg of sodium borohydride in 5 ml of methanol cooled at −20° C under nitrogen was added a solution of 60 mg of 3-(3'-hydroxy-1'-trans-octenyl)-2-(6'-carbomethoxy-2'-cis-hexenyl)-indan-1-one in 5 ml of methanol.

After 30 minutes, the reaction solution was quenched by dropwise addition of 5 ml of acetic acid and the mixture was concentrated under reduced pressure.

The resulting residue was dissolved in ethyl acetate and the organic layer was washed with aqueous sodium bicarbonate, water and brine, dried over magnesium sulfate and evaporated to give 55 mg of 3-(3'-hydroxy-1'-trans-octenyl)-2-(6'-carbomethoxy-2'-cis-hexenyl)-indan-1-ol.

IR$\gamma_{max}^{film}$: 3400, 1740, 1600 cm$^{-1}$

EXAMPLE 13

To a stirred solution of indene (45 g) in dry ether (300 ml) cooled to −60° under nitrogen, was added 250 ml of 15% solution of n-butyllithium in n-hexane.

After 30 minutes of additional stirring at −50° C, to this was added a solution of 150 g of 1,2-dibromoethane in 130 ml of ether at same temperature. After stirring for another 3 hrs. at 0° C. The reaction mixture was poured into aqueous ammonium chloride and ice-water and extracted with ether. The ether layer was dried over magnesium sulfate, and concentrated under reduced pressure. The residue was purified by distillation to give 42 g of 1-(2'-bromoethyl)-indene b.p. 97° C/0.1 mmHg To 1.1 g of magnesium metal, was added a solution of 9.9 g of haloalkyl indene prepared above in 100 ml of dry ether with stirring.

Stirring was continued for 30 minutes and then cooled to 15° C. To this mixture, was added a solution of 5 g of freshly distilled n-hexanol in 20 ml of ether. The resulting mixture was stirred for another 3 hrs., then poured into aqueous ammonium chloride and extracted well with ether. The ether extracts were combined, washed with brine, dried over magnesium sulfate and evaporated to give a residue, which was chromatographed on silica gel to afford 6.2 g of 1-(3'-hydroxyoctyl)-indene as yellow oil.

A mixture of 120 ml of acetic acid, 60 ml of acetic anhydride, 7.0 g of 1-(3'-hydroxy-octyl)-indene and 26.8 g of manganic acetate was heated to reflux for 30 minutes under nitrogen. After cooling to room temperature, the manganese acetate was removed by filtration and washed well with ethylacetate. The filtrate was concentrated under reduced pressure. The residue dissolved in ethyl acetate was washed with water, and aqueous sodium bicarbonate, dried over magnesium sulfate and concentrated to give a crude mixture, which was chromatographed on silica-gel to afford 5.1 g of 1-hydroxy-3-(3'-acetoxy-octyl)-2-indan acetic acid-$\gamma$-lactone as yellow oil.

IR$\gamma_{max}^{film}$: 1780, 1735, 1605 cm$^{-1}$

Following the procedures of Example 13, 3-(3'-methyl-3'-hydroxy-octyl)-2-indan acetic acid-$\gamma$-lactone was obtained.

IR$\gamma_{max}^{film}$: 3400, 1775, 1605, 1160, 1020 cm$^{-1}$

EXAMPLE 14

To a solution of 526 mg of 1-hydroxy-3-(3'-acetoxy-octyl)-2-indan acetic acid-$\gamma$-lactone in 50 ml of dry toluene cooled to −60° C under nitrogen was added dropwise diisobutylaluminium hydride (1.1 g) in toluene. Stirring and cooling was continued for 1 hr., and then aqueous ammonium chloride was cautiously added. The mixture was filtered through Celite and the filtrate was washed with brine, dried and concentrated to give 440 mg of 1-hydroxy-3-(3'-hydroxy-octyl)-indan-2-acetoaldehyde-$\gamma$-lactol as yellow oil.

IR$\gamma_{max}^{film}$: 3400, 1600, 1025 cm$^{-1}$

A suspension of 65% sodium hydride (443 mg) and 8 ml of dimethyl sulfoxide was stirred for 1.5 hrs. at 70° C under nitrogen and cooled to ambient temperature.

To this solution was added 2.66 g of 4-carboxy-n-butyl-triphenylphosphonium bromide with 7 ml of dimethyl sulfoxide. After stirring for 5 minutes, to this was added a solution of 440 mg of 1-hydroxy-3-(3'-hydroxy-octyl)-indan-2-acetoaldehyde $\gamma$-lactol in 10 ml of dimethylsulfoxide and the resulting mixture was allowed to stir vigorously for 2 hrs. at room temperature.

The reaction mixture was quenched by addition to a mixture of ice-water and ether. After equilibration, the organic phase was washed with 1 N sodium hydroxide and water. The aqueous washings were combined and carefully acidified with diluted hydrochloric acid. The aqueous phase was extracted well with ethylacetate. The organic extract was washed with water, dried and concentrated under reduced pressure. The resulting residue was dissolved in tetrahydrofuran and treated with excess ethereal diazomethane.

After evaporation, the residue was chromatographed on silica gel to give 278 mg of 3-(3'-hydroxy-octyl)-2-(6'-carbomethoxy-2'-cis-hexenyl)-indan-1-ol as faint yellow oil.

IR$\gamma_{max}^{film}$: 3400, 1735, 1600 cm$^{-1}$

Following the procedures of Example 14, 3-(3'-methyl-3'-hydroxy-octyl)-2-(6'-carbomethoxy-2'-cis-hexenyl)-indan-1-ol was obtained.

IR$\gamma_{max}^{film}$: 3500, 1740, 1605 cm$^{-1}$

EXAMPLE 15

A mixture of 100 mg of 3-(3'-hydroxy-octyl)-2-(6'-carbomethoxy-2'-cis-hexenyl)-indan-1-ol and 30 mg of 5% palladium on carbon in 10 ml of ethanol was stirred for 2 hrs. at room temperature under 1 atm of hydrogen. The mixture was filtered through Celite, washing well with ethanol. The filtrate was concentrated to give 95 mg of 3-(3'-hydroxy-octyl)-2-(6'-carbomethoxy-hexyl)-indan-1-ol as yellow oil.

IR$\gamma_{max}^{film}$: 3400, 1730, 1600 cm$^{-1}$

EXAMPLE 16

1 g of active manganese dioxide was added to a solution of 100 mg of 3-(3'-hydroxy-octyl)-2-(6'-carbomethoxy-2'-cis-hexenyl)-indan-1-ol in dry benzene and the resulting mixture was refluxed for 6 hrs. The mixture was filtered through Celite and the filtrate was evaporated to give 90 mg of 3-(3'-hydroxy-octyl)-2-(6'-carbomethoxy-2'-cis-hexenyl)-indan-1-one as faint yellow oil.

IR$\gamma_{max}^{film}$: 3400, 1735, 1710, 1605 cm$^{-1}$

Following the procedures of Example 16, 3-(3'-hydroxy-octyl)-2-(6'-carbomethoxy-hexyl)-indan-1-one was obtained.

IR$\gamma_{max}^{film}$: 3400, 1735, 1710, 1600 cm$^{-1}$

EXAMPLE 17

A mixture of 121 mg of 3-(3'-hydroxy-octyl)-2-(6'-carboxy-2'-cis-hexenyl)-indan-1-ol and 2 g of active manganese dioxide in 20 ml of dry chloroform was stirred over night at room temperature. The resulting mixture was filtered through Celite and the filtrate was concentrated to give 94 mg of 3-(3'-hydroxy-octyl)-2-(6'-carboxy-2'-cis-hexenyl)-indan-1-one as light yellow oil.

IR$\gamma_{max}^{film}$: 3400, 2650, 1710, 1605 cm$^{-1}$

Following the procedures of Example 17, 3-(3'-hydroxy-octyl)-2-(6'-carboxy-hexyl)-indan-1-one was obtained as oil.

IR$\gamma_{max}^{film}$: 3400, 2650, 1710, 1605 cm$^{-1}$

EXAMPLE 18

A mixture of 65 mg of 3-(3'-hydroxy-1'-trans-octenyl)-2-(6'-carbomethoxy-2'-cis-hexenyl)-indan-1-one, 10 ml of a solution of methanol-water (10:1) and 200 mg of potassium carbonate was stirred overnight at room temperature, and then concentrated under reduced pressure. To this resulting residue was added water and ether and the organic phase was washed with water after equilibration. The aqueous washings were combined and carefully acidified with 2 M potassium bisulfate in the presence of ether. After equlibration, the aqueous phase was extracted well with ether. The organic extracts were combined, dried over magnesium sulfate and evaporated to give 58 mg of 3-(3'-hydroxy-1'-trans-octenyl)-2-(6'-carboxy-2'-cis-hexenyl)-indan-1-one as light yellow oil IR$\gamma_{max}^{film}$: 3400, 2650, 1710, 1605 cm$^{-1}$

What is claimed is:

1. A compound of the formula,

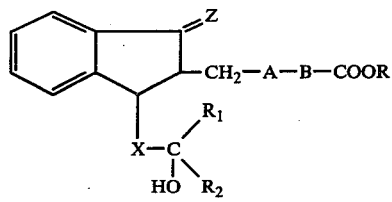

wherein A and X are each ethylene or vinylene; B is $C_{2-4}$ alkylene; R and $R_2$ are each hydrogen or $C_{1-4}$ alkyl; $R_1$ is $C_{1-8}$ alkyl and $<C = Z$ is $<C = O$ or

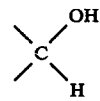

2. A compound of the formula,

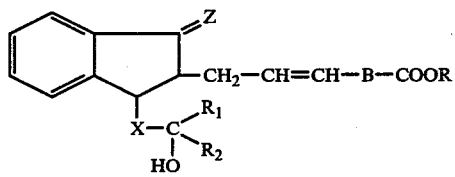

wherein X is ethylene or vinylene; B is $C_{2-4}$ alkylene; R and $R_2$ are each hydrogen or $C_{1-4}$ alkyl; $R_1$ is $C_{1-8}$ alkyl; and $<C = Z$ is $<C = O$ or

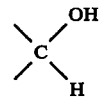

3. A compound of the formula,

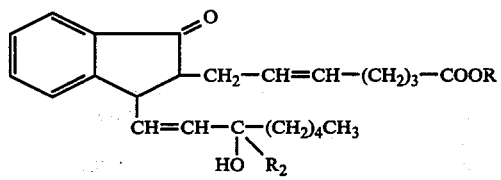

wherein R and $R_2$ are each hydrogen $C_{1-4}$ alkyl.

4. A pharmaceutical composition comprises as an active ingredient a hypotensively effective amount of at least one of the compounds claimed in claim 1 with at least one pharmaceutically inert carrier or diluent.

5. Method of treating hypertension comprising administering a hypotensively effective amount of a compound according to claim 1.

6. A compound according to claim 1 which is 3-(3'-hydroxy-octyl)-2-(6'-carboxy-2'-cis-hexenyl)-indan-1-one.

* * * * *

UNITED STATES PATENT OFFICE
CERTIFICATE OF CORRECTION

Patent No. 4,125,731　　　　　　　　　Dated　November 14, 1978

Inventor(s)　Akihiko SUGIE et al.

It is certified that error appears in the above-identified patent and that said Letters Patent are hereby corrected as shown below:

Column 7, Chart B, between formulae (15) and (16) insert an arrow showing the course of reaction as follows:

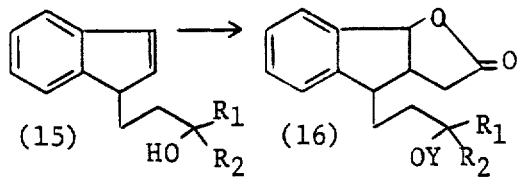

Column 8, top of page, before formula (II) insert an arrow showing the course of reaction as follows:

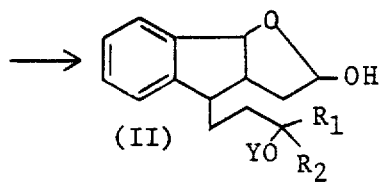

UNITED STATES PATENT AND TRADEMARK OFFICE
CERTIFICATE OF CORRECTION

PATENT NO. : 4,125,731
DATED : November 14, 1978
INVENTOR(S) : Akihiko Sugie et al.

It is certified that error appears in the above-identified patent and that said Letters Patent are hereby corrected as shown below:

Column 8, line 44, delete "TM9" and insert -- TIS --.

Signed and Sealed this

Seventh Day of August 1979

[SEAL]

Attest:

LUTRELLE F. PARKER
Attesting Officer   Acting Commissioner of Patents and Trademarks